United States Patent
Diederichs et al.

(10) Patent No.: US 8,637,688 B2
(45) Date of Patent: Jan. 28, 2014

(54) TOPICAL DOSAGE FORM COMPRISING TRI-SUBSTITUTED GLYCEROL COMPOUNDS

(76) Inventors: Julia Diederichs, Munich (DE); Wolfgang Richter, Munich (DE); Lutz Weber, Germering (DE)

( * ) Notice: Subject to any disclaimer, the term of this patent is extended or adjusted under 35 U.S.C. 154(b) by 513 days.

(21) Appl. No.: 12/520,368

(22) PCT Filed: Nov. 9, 2007

(86) PCT No.: PCT/EP2007/062179
§ 371 (c)(1),
(2), (4) Date: Dec. 16, 2009

(87) PCT Pub. No.: WO2008/074573
PCT Pub. Date: Jun. 26, 2008

(65) Prior Publication Data
US 2010/0179226 A1      Jul. 15, 2010

Related U.S. Application Data

(60) Provisional application No. 60/875,962, filed on Dec. 20, 2006.

(51) Int. Cl.
| | | |
|---|---|---|
| C07F 9/10 | (2006.01) |
| C11D 1/28 | (2006.01) |
| A61K 31/685 | (2006.01) |
| C07C 305/02 | (2006.01) |

(52) U.S. Cl.
USPC ............... 554/80; 554/96; 514/78; 514/76; 514/77; 514/786; 514/642; 558/32; 558/31; 558/29

(58) Field of Classification Search
None
See application file for complete search history.

(56) References Cited

U.S. PATENT DOCUMENTS

| | | | | |
|---|---|---|---|---|
| 4,837,023 A | * | 6/1989 | Eibl | 424/439 |
| 5,266,564 A | * | 11/1993 | Modolell et al. | 514/77 |
| 5,762,958 A | * | 6/1998 | Mayhew et al. | 424/450 |
| 6,514,519 B1 | * | 2/2003 | Nagler | 424/439 |
| 6,583,127 B1 | * | 6/2003 | Gajate et al. | 514/77 |
| 7,998,945 B2 | * | 8/2011 | Braxmeier et al. | 514/76 |

FOREIGN PATENT DOCUMENTS

| | | | | |
|---|---|---|---|---|
| DE | 19829448 | * | 10/2000 | |
| WO | WO 94/08565 | * | 4/1994 | A61K 9/127 |

OTHER PUBLICATIONS

Jendrossek, V. et al., Membrane Targeted Anticancer Drugs: Potent inducers of apoptosis and putative radiosensitisers, 2003, Curr. Med. Chem.—Anti-Cancer, vol. 3, No. 5, pp. 343-353.*
Pinchuk, A.N. et al., Synthesis of Alkyl Glycerophospholipids through 1-O-benzyl-2-O-methyl-rac-glycerol, 1992, Pharmaceutical Chemistry Journal, Consultant Bureau, vol. 26, pp. 174-176.*
DE 4000084 A1, Wiebeck, D. et al., 1991, English translation pp. 1-9.*
Nagler, 2000, English Translation of DE 19829448, 12 pages.*
Gennaro, A. et al., Remington's Pharmaceutical Sciences, 1985, Mack Printing Co., 17th edition (47 pages).*
Casanova, M.L., et al., Inhibitin of skin tumor growth and angiogenesis in vivo by activaitn f cannabinoid receptors, 2003, The Journal of Clinical Investigation, vol. 111, No. 1, pp. 43-50.*
Furuya, M., et al., Pathophysioilogy of tumor neovascularization, 2005, Vascular Health and Risk Management, 1(4), pp. 277-290.*
Girault, A., et al., Targeting SKCa channels in cancer: potential new therapeutic approaches, 2012, Current Medicinal Chemistry, vol. 19, No. 5, pp. 697-713.*
Potier, M., et al., Identification of SK3 channel as a new mediator of breast cancer cell migration, 2006, Molecular Cancer Therapeutics, vol. 5, No. 11, 9 pages.*
Vogler, W.R., et al., The anticancer drug edelfosine is a potent inhibitor of neovascularizatin in vivo, 1998, Cancer Investigation, 16(8), pp. 549-553.*

* cited by examiner

Primary Examiner — Yate K Cutliff
(74) Attorney, Agent, or Firm — K&L Gates LLP

(57) ABSTRACT

The present invention relates to pharmaceutical dosage forms for topical administration comprising a tri-substituted glycerol compound or a pharmaceutically acceptable salt thereof. The invention also relates to a corresponding method for preparing such dosage forms as well as to their use as medicaments for the treatment of cancer and immune diseases.

20 Claims, No Drawings

TOPICAL DOSAGE FORM COMPRISING TRI-SUBSTITUTED GLYCEROL COMPOUNDS

CROSS-REFERENCE TO RELATED APPLICATIONS

This application claims the benefit of International Patent Application No. PCT/EP2007/062179 filed on Nov. 9, 2007 and U.S. Provisional Patent Application No. 60/875,962 filed on Dec. 20, 2006, the disclosures of each of which are incorporated by reference herein.

The present invention relates to pharmaceutical dosage forms for topical administration comprising a tri-substituted glycerol compound or a pharmaceutically acceptable salt thereof. The invention also relates to a corresponding method for preparing such dosage forms as well as to their use as medicaments for the treatment of cancer and immune diseases.

The tri-substituted glycerol compounds used in the present invention belong to the class of synthetic ether-linked alkyl-lysophospholipids, which are known to have an anti-cancerogenic activity, why they are also collectively named "anti-tumor ether lipids" (reviewed, e.g., by Arthur, G., and Bittman, R. (1998) Biochim. Biophys. Acta 1390, 85-102; Jendrossek, V., and Handrick, R. (2003) Curr. Med. Chem. Anti-Canc. Agents 3, 343-353; Mollinedo, F. et al. (2004) Curr. Med. Chem. 11, 3163-3184).

Aside from their anti-tumor activity, these ether lipids are believed to be involved in a variety of other physiological processes such as inflammation, the immune response or allergic reactions. Some ether lipids have been suggested as candidate compounds for the treatment of various immune diseases (cf., for example, the International Patent Applications WO 87/01257 and WO 90/14829, respectively).

1-O-octadecyl-2-O-methyl-glycero-3-phosphocholine (also referred to as ET-18-OCH3, AP-121 or edelfosine) is considered to be the prototype of the anti-tumor ether lipids. 1-O-octadecyl-2-O-methyl-glycero-3-phosphocholine represents a synthetic analogue of the platelet activating factor (PAF; 1-O-alkyl-2-acetyl-sn-glycero-3-phosphocholine), a potent phospholipid activator and mediator of many leukocyte functions, including platelet aggregation, inflammation, and anaphylaxis. Unlike most conventional chemotherapeutic drugs, these synthetic ether lipids do not directly target cellular DNA but rather affect the plasma membrane lipid composition and/or interfere with various signal transduction pathways. Thus, their mode of action does not depend on the presence of particular cellular receptors or is it cell cycle-dependent.

Cancer chemotherapy generally aims to slow the growth of, or destroy, cancer cells while avoiding collateral damage to surrounding cells and tissues. Consequently, the most effective anticancer agents are those that are able to selectively target cancer cells while leaving normal cells relatively unaffected. Synthetic ether-lipids have been shown to be effective as tumor agents, for example, in order to decrease or to stop tumor progression, i.e. to stabilize the "status quo" of the condition, or even to reduce the size of tumors in mammals.

1-O-octadecyl-2-O-methyl-glycero-3-phosphocholine has been reported to be suitable for the treatment of particular types of tumors such as brain tumors or mamma carcinomas (cf., for example, the German Patent DE 2619686 as well as the International Patent Applications WO 99/59599 and WO 00/01392, respectively).

Several mechanisms of action have been proposed for the toxicity of ether-lipids towards cancer cells, including the cells' lack of alkyl cleavage enzymes. The resultant inability to hydrolyze the ether-lipids leads to their intracellular accumulation and to consequent damage to cell membrane lipid organization. Other potential mechanisms of ether-lipid action include effects on levels of intracellular protein phosphorylation, and disruption of cellular lipid metabolism. Normal cells typically possess the means to avoid or overcome the potentially toxic effects of ether-lipids, while cancer cells do not.

Although anti-tumor activity of these synthetic ether lipids has been experimentally proven in several animal tumor models, their clinical use is often hampered by systemic cytotoxic effects including hemolysis that are particularly observed in the gastrointestinal tract but also inter alia in lung, liver or kidney. Accordingly, the route of administration of such ether lipids appears a critical issue.

Currently, in the vast majority of clinical trials on synthetic ether lipids the compounds are administered to patients orally or by using the intravenous route. In this context, it was found that the intravenous administration of a liposomal formulation and a lipophilic oil-in-water emulsion, respectively, is advantageous as compared to the free compound in order to improve therapeutic efficacy while reducing nonspecific toxicity in vivo (see, for example, Ahmad, I. et al. (1997) Cancer Res. 57, 1915-1921 as well as International Patent Application WO 91/09590).

However, it is also known in the art that certain ether phospholipid and carbamoyl salts while exhibiting benefits to a patient as competitive inhibitors of PAF or tumor growth with single or repeated injections, cause detrimental effects in the area of the injection. These detrimental effects are evident as lysis of red blood cells, severe edema, inflammation, and injection site-necrosis. These adverse effects are also called "detergent" effects. Where repeated injections are required, these detrimental effects are particularly disadvantageous as they render the sites of administration unsuitable and require fresh sites. Since the number of suitable sites on a patient is limited, it would be highly desirable to avoid said detrimental effects associated with intravenous administration of 1-O-octadecyl-2-O-methyl-glycero-3-phosphocholine.

Rather recently, it has been shown that in order to limit systemic side effects it is also possible to administer synthetic ether lipids orally together with a liquid drinkable vehicle. In the International Patent Application WO 99/59599, it is described that 1-O-octadecyl-2-O-methyl-glycero-3-phosphocholine can be administered together with water- or milk-based vehicles containing at least 3% (w/w) fat and/or protein. It is tempting to speculate that an efficient binding of 1-O-octadecyl-2-O-methyl-glycero-3-phosphocholine to the proteins and/or other lipids "mask" the ether-lipid thus resulting in a reduction of adverse side effects.

Nevertheless, in 10-20% of the patients treated with such water- and/or milk-based vehicles significant gastrointestinal incompatibilities (corresponding to WHO toxicity grades III and IV, respectively) have been observed that are associated with loss of appetite, nausea and/or vomiting, diarrhea, constipation or the like (see, for example, Drings, P. et al. (1992) Onkologie 15, 375-382).

Therefore, alternative dosage forms also allowing for other routes of administration would be desirable. This is of particular relevance for certain indications such as the treatment of skin cancer, skin metastases/progressive skin lesions of other types of cancer (e.g., breast cancer) or inflammatory and/or immune diseases affecting the skin (such as systemic lupus erythematosis or polyarthritis) where an oral or intravenous application may not be the first choice in order to administer the active ingredients locally or systemically directly to the affected site(s) to be treated with the gastrointestinal tract being by-passed. In such cases, the therapeutic use of topically administrable pharmaceutical preparations would be indicated.

The only approved topical dosage form comprising an ether lipid that is currently available is a 6% solution comprising hexadecylphosphocholine (also referred to as miltefosine, a compound not having a glycerol backbone) for the treatment of cutaneous metastases from breast cancer (see, e.g., Smorenburg, C. H. et al. (2000) Anticancer Drugs 11, 825-828; Leonard, R. et al. (2001) *J. Clin. Oncol.* 19, 4150-4159). Furthermore, miltefosine has shown efficacy against visceral leishmaniasis (see, e.g., Jha, T. K. et al. (1999) *N. Engl. J. Med.* 341, 1795-1800). However, in general only about one third of the patients treated showed a beneficial response to the medicament, probably due to an inadequate solubility of the amphiphilic active ingredient or by an impaired penetration of such formulations through the skin barrier. Furthermore, the total amount of active ingredient present in the dosage form may not be sufficient to achieve the desired pharmaceutical effect. In the clinical trials performed so far, the active ingredient has been applied in an average dose rate of 0.3 mg/cm$^2$ skin area. On the other hand, however, significant skin irritations (manifested in form of redness, itching, cauterization or the like) are often observed shortly upon administration.

Thus, there still remains a need for pharmaceutical dosage forms for topical administration comprising 1-O-octadecyl-2-O-methyl-glycero-3-phosphocholine or a related tri-substituted glycerol compound that overcome the above limitations. In particular, there is a need for a dosage form, which allows for an easy and convenient local administration of high doses of the compound while providing the required pharmaceutical efficacy and/or bioavailability of the active ingredient with respect to the treatment of cancer and other diseases.

Accordingly, it is an object of the present invention to provide such a pharmaceutical dosage form for topical administration.

This object is achieved by the pharmaceutical dosage form having the features of independent claim 1 as well as the method for preparing such a pharmaceutical dosage form having the features of independent claim 21. Some of the preferred embodiments of the present invention are defined by the subject matter of the dependent claims.

According to the present invention, it has been found that it is possible to formulate topical dosage forms containing tri-substituted glycerol compounds such as 1-O-octadecyl-2-O-methyl-glycero-3-phosphocholine which are suitable for treating cancer or immune diseases, and which not only allow for a convenient taking of the medicament but also for an efficient penetration/uptake of the active ingredient when applied to the skin. Surprisingly, it was found that by using the inventive dosage forms concentrations of 100 mg active ingredient per gram of the dosage form (i.e. 10% (w/w)) or even more can be administered to a patient with high efficacy, thus resulting in an improved bioavailability of the active ingredient.

In the context of the present invention any numerical value indicated is typically associated with an interval of accuracy that the person skilled in the art will understand to still ensure the technical effect of the feature in question. As used herein, the deviation from the indicated numerical value is in the range of ±10%, and preferably of ±5%.

In a first aspect, the present invention relates to pharmaceutical dosage forms for topical administration comprising a tri-substituted glycerol compound according to formula (I)

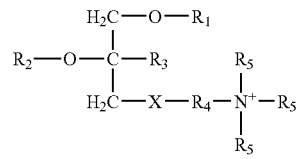

or an enantiomer or diastereomer or a pharmaceutically acceptable salt thereof and at least one pharmaceutically acceptable excipient, wherein X is selected from the group consisting of phosphate and sulfate;

$R^1$ is selected from the group consisting of $C_{16}$-$C_{20}$ alkyl;

$R^2$ is selected from the group consisting of $C_1$-$C_3$ alkyl and $C_1$-$C_3$ hydroxyalkyl;

$R^3$ is selected from the group consisting of hydrogen and $C_1$-$C_3$ alkyl;

$R^4$ is selected from the group consisting of $C_1$-$C_3$ alkyl and $C_3$-$C_6$ cycloalkyl; and $R^5$ is selected from the group consisting of hydrogen and methyl.

The terms "$C_n$ alkyl", "$C_n$ hydroxyalkyl", and "$C_n$ cycloalkyl", as used herein, denote an alkyl group, a hydroxyalkyl group or a cycloalkyl group having a number of n carbon atoms, respectively. For example, the term "$C_{18}$ alkyl" refers to an alkyl group having 18 carbon atoms. The alkyl groups or hydroxyalkyl groups according to the invention may be straight or branched.

The tri-substituted glycerol compounds of formula (I) have one or more asymmetric centers and thus they can exist as enantiomers or diastereomers. Thus, the pharmaceutical solid dosage forms according to the present invention may comprise either one or more separate individual isomers (such as the L form and the D form) or mixtures of isomers, preferably racemic mixtures.

In some embodiments of the invention, the tri-substituted glycerol compounds of formula (I) are present in the dosage form as pharmaceutically acceptable salts. Such salts may comprise any pharmaceutically acceptable anion "neutralizing" the positive charge of the nitrogen (e.g. chloride, bromide or iodide) or any pharmaceutically acceptable cation "neutralizing" the negative charge of the phosphate or sulfate moiety (e.g. sodium or potassium cations).

In a particular preferred embodiment of the present invention, the pharmaceutical dosage form comprises a tri-substituted glycerol compound according to formula (I), wherein X is phosphate, $R_1$ is —$(CH_2)_{17}$—$CH_3$, $R_2$ is $CH_3$, $R_3$ is H, $R_4$ is —$(CH_2)_2$—, and $R_5$ is $CH_3$.

According to the present invention, it is to be understood that the tri-substituted glycerol compound is present in the pharmaceutical dosage form in any amount being effective to achieve the desired pharmacological effect such as to stop tumor progression or to induce an apoptotic effect in tumor cells when administered to a patient. Effective amounts are generally chosen in accordance with a number of factors, e.g., the age, size and general condition of the patient and the medical condition being treated, and determined by a variety of means, for example, dose ranging trials, well known to, and readily practiced by persons of ordinary skill in art given the teachings of this invention.

Typically, in the pharmaceutical dosage form according to the present invention the amount of the tri-substituted glycerol compound according to formula (I) is at least 2% (w/w), that is at least 2% by weight based on the total weight of the dosage form. This amount corresponds to a concentration of at least 20 mg/g of the dosage form. Preferably, the amount of the tri-substituted glycerol compound according to formula (I) in the pharmaceutical dosage form is at least 5% (w/w), more preferably at least 10% (w/w), and most preferably at least 15% (w/w). Thus, according to the present invention it may also be possible to formulate topical dosage forms comprising at least 20% (w/w) or at least 25% (w/w) of the tri-substituted glycerol compound according to formula (I) or even higher amounts.

The daily dosage of the tri-substituted glycerol compound according to formula (I) administered to a patient is less than 1200 mg, typically less than 900 mg, preferably in the range of 30 to 600 mg, more preferably in the range of 40 to 400 mg, and most preferably in the range of 50 to 350 mg.

The pharmaceutical dosage form is applied to the skin in a dose rate of 0.01 to 10 mg tri-substituted glycerol compound/$cm^2$ skin area, preferably in a dose rate of 0.05 to 5 $mg/cm^2$ skin area, and particularly preferably in a dose rate of 0.2 to 1 mg tri-substituted glycerol compound/$cm^2$ skin area.

The daily dosage of the tri-substituted glycerol compound may be administered as a single dose or in multiple doses such as two or three individual doses administered during the day, e.g. in the morning, at noon, and at night. Within the scope of the present invention, it may be possible to apply the pharmaceutical dosage form comprising the tri-substituted glycerol compound according to formula (I) to the skin by means of an applicator or dispenser device to ensure administration of a particular amount of the compound to a given skin area (that is to avoid overdosing of the dosage form).

The tri-substituted glycerol compound according to formula (I) may be present in the pharmaceutical solid dosage form as a single active ingredient or in combination with at least one other active ingredient such as chemotherapeutics or monoclonal antibodies.

In some embodiments of the invention, the total amount of lipids in the pharmaceutical dosage form is at last 50% (w/w), i.e. 50% by weight based on the total weight of the dosage form. Preferably, the total amount of lipids in the pharmaceutical dosage form is at last 25% (w/w), and particularly preferably it is at last 10% (w/w).

The term "lipid", as used herein, refers to any hydrocarbon-containing organic compounds that they are soluble in non-polar solvents and are relatively insoluble in water. Such compounds include any naturally occurring or synthetically produced fatty acids (i.e. saturated or unsaturated aliphatic monocarboxylic acids having the general formula $CH_3(CH_2)_nCOOH$) as well as glycerides (i.e. lipids possessing a glycerol core structure with one or more fatty acyl groups, which are fatty acid-derived chains attached to the glycerol backbone by ester linkages).

Examples of saturated fatty acids include inter alia butyric acid, caprylic acid, palmitic acid, and stearic acid. Examples of unsaturated acids include inter alia oleic acid and linoleic acid. The term "glycerides" includes mono-, di-, and triglycerides. Examples of such glycerides are inter alia phospholids (e.g., phosphatidyl choline, phosphatidyl serine, and diphosphatidyl glycerol), sphingolipids (e.g., ceramide, and sphongomyelin) and sterols such as cholesterol. The lipids may be present in free form or included in a composite such as animal fats (e.g., cod-liver oil), vegetable fats and oils (e.g., cocoa butter, shea butter, olive oil, safflower oil, peanut oil, sesame oil, and sweet almond oil), waxes (such as beeswax, paraffin wax, and wool wax), Vaseline® (petroleum jelly, petrolatum) or the like.

In some embodiments of the present invention, the pharmaceutical dosage form does not comprise liposomes, even though lipids may be present in the formulation. Within the scope of the invention, the term "liposome" refers to a (spherical) vesicle with an aqueous (hydrophilic) core enclosed by one or more bilayers of lipids, typically of phospholipids. Such bilayer is composed of two opposing layers of lipid molecules arranged in such a way that their hydrophobic hydrocarbon tails face one another, while their charged hydrophilic head regions face the aqueous solutions on either side of the membrane (reviewed, e.g., in Torchilin, V., and Weissig, V. (eds.) (2003) *Liposomes—a practical approach*, 2nd ed., Oxford University Press, New York, N.Y.). In contrast, spheres not comprising an aqueous phase in their interior that is surrounded by a monolayer of phospholipids or other amphiphilic compounds are called micelles. Micelles may be present in the pharmaceutical dosage forms according to the invention.

The pharmaceutical dosage form according to the present invention may be any therapeutically effective pharmaceutical dosage form for topical administration. Examples of such pharmaceutical dosage forms include inter alfa solutions, suspensions, dispersions, tinctures, gels, topical sprays, topical foams, gels, water-in-oil emulsions such as ointments, and oil-in water emulsions such as creams, lotions, and balms, with gels and oil-in water emulsions being preferred.

The term "gel", as used herein, refers to a colloidal system in which a porous network of interconnected nanoparticles spans the volume of a liquid medium. In general, gels are apparently solid, jelly-like materials. Both by weight and volume, gels are mostly liquid in composition and thus exhibit densities similar to liquids, however have the structural coherence of a solid.

In a particularly preferred embodiment of the invention, the pharmaceutical dosage form is a hydrogel. A "hydrogel", as used herein, refers to a gel made of one or more cross-linked water-swellable (hydrophilic) gel-forming polymers such as polysaccharides or polyacrylic acid derivatives. The gel-forming polymers may be naturally occurring polymers, synthetic polymers or mixtures thereof. Hydrogels may comprise more than 99% water. When applied to the skin the water bound in such a hydrogel does not evaporate as fast as from a solution. Due to the thus prolonged contact period the skin becomes moistened which, in turn, results in an improved susceptibility for the uptake of active ingredients present in the hydrogel (i.e. an increased penetration through the skin). This phenomenon is also referred to as "occlusion effect".

Typically, such gel-forming polymers have an average molecular weight of 1000 to 50000 Dalton, preferably of 1000 to 30000 Dalton. A hydrogel of the invention may also be characterized by its rheological properties. Typically, it has an initial shear modulus of 0.005 to 200 kPa, preferably of 0.05 to 100 kPa. The "shear modulus", also referred to as the modulus of rigidity, is defined as the ratio of shear stress to the shear strain and provides a measure for the strength of a given material. Additionally or alternatively, it may also be possible to characterize a hydrogel by its flow behavior such as by its viscosity coefficient $\eta$ as determined by the flow models of Bingham, Casson, Herschel-Bulkley and Ostwald, respectively, all of them well known in the art (see, e.g. Gosh, T. K. et al. (1997) *Transdermal and topical drug delivery systems*. CRC Press, Boca Raton, Fla., USA; Fairclough, J. P. A., and Norman A. I. (2003) *Annu. Rep. Prog. Chem., Sect. C: Phys. Chem*. 99, 243-276).

In another preferred embodiment, the hydrogel comprises one or more gel-forming polymers in a total amount of 0.1% to 15% (w/w) based on the total weight of the hydrogel. Particularly preferably, the one or more gel-forming polymers are selected from the group consisting of cellulose derivatives, polyacrylic acid derivatives, and gums. Examples of cellulose derivatives include inter alia methylcellulose, ethylcellulose, hydroxyethyl cellulose, and carboxymethyl cellulose. Examples of polyacrylic acid derivatives include inter alia polyacrylic acid, polymethylacrylate, and polyethylacrylate. Examples of gums (also referred to as "rubbers") include inter alia agar, alginic acid, glucomannan, arabic gum, sodium alginate, and tragacanth.

In some embodiments, the inventive hydrogel does not comprise any lipids, that is it is a "fat-free" hydrogel. Typically, the hydrogels of the invention comprise at least 75% (w/w) water, and preferably they comprise at least 80% (w/w) water.

In other preferred embodiments of the invention, the pharmaceutical dosage form is an oil-in-water emulsion. The term "oil-in-water emulsion", as used herein, refers to formulations which are composed of small droplets of a lipid phase (e.g., an oil) dispersed in a continuous aqueous phase. An "emulsion" is a mixture of two immiscible (i.e. not mixable) substances. One substance (the dispersed phase) is dispersed (i.e. distributed) in the other (the continuous phase) by the presence of one or more emulsifying agents. In general, oil-in-water emulsions are more comfortable and pharmaceutically/cosmetically acceptable as compared to water-in-oil emulsions (such as an ointment) as they are less greasy when applied on the skin and more easily washed off when using water. By employing such an oil-in-water emulsion the penetration of amphiphilic compounds such as the tri-substituted glycerol compounds of the invention through the skin is improved as compared to formulations having only an aqueous phase, since the presence of a lipid phase is assumed to aid in crossing the hydrophobic core of biological membranes.

Particularly preferred oil-in-water-emulsions of the invention are selected from the group consisting of creams, lotions, and balms. These formulations primarily differ with regard to their respective viscosities. A cream is a semi-solid emulsion, that is it has a medium viscosity. In contrast, a lotion is a low-to medium-viscosity preparation intended for application to unbroken skin. Finally, a balm (also referred to as liniment) has a similar viscosity as a lotion (i.e. being significantly less viscous than a cream) but unlike a lotion a balm is applied with friction, that is a liniment is always rubbed in.

Preferably, the oil-in-water emulsions according to the invention comprises one or more emulsifiers in a total amount of 0.5% to 15% (w/w) based on the total weight of the dosage form. Whether an emulsion turns into a water-in-oil emulsion or an oil-in-water emulsion depends on the volume fraction of both phases and on the type of emulsifier. Generally, the Bancroft rule applies: emulsifiers and emulsifying particles tend to promote dispersion of the phase in which they do not dissolve very well. In other words, the phase in which an emulsifier is more soluble constitutes the continuous phase. Thus, for the preparation of oil-in-water emulsions water-soluble emulsifiers are preferred.

Particularly preferably, the one or more emulsifiers are selected from the group consisting of sorbitan esters (also referred to as Span®), polyoxyethylene sorbitan esters (also referred to as polysorbates; Tween®), and glyceryl esters. Examples of sorbitan esters include inter alia sorbitan monooleate, sorbitan monostearate, sorbitan monolaurate, sobitan trioleate, and sorbitan tristearate. Examples of polyoxyethylene sorbitan esters include polyethylene glycol (PEG) sorbitan esters such as inter alia PEG-(5)-sorbitan monooleate, PEG-(4)-sorbitan monostearate, PEG-(4)-sorbitan monolaurate, PEG-sobitan trioleate, and PEG-sorbitan tristearate. Examples of glyceryl esters include inter alia glyceryl monostearate, glyceryl monolaurate, and glyceryl tristearate.

Other emulsifiers that can be used in the present invention include inter alia lecithin, cholesterol, phosphatidylglycerols, alkyl alcohols, poloxamers (also referred to as Pluronic®/Synperonic®), poloxamin (also referred to as Tetronic®), sodium laurylsulfate, sodium cetylstearylsulfate, and potassium oleate.

The pharmaceutical dosage forms of the present invention comprise at least one pharmaceutically acceptable excipient. The term "pharmaceutically acceptable excipient", as used herein denotes any substance used for the preparation of pharmaceutical dosage forms such as carrier materials, wetting agents, preservatives, buffers, solvents or solubilizers, agents for achieving a depot effect, and other adjuvants, all of them well known in the art (cf. the references cited below).

All these topical pharmaceutical dosage forms as well as methods for their preparation are well established in the art (see, for example, Niedner, R., and Ziegenmeyer, J. (1997) *Dermatika. Therapeutischer Einsatz, Pharmakologie and Pharmazie*. Wissenschaftliche Verlagsgesellschaft mbH, Stuttgart, Germany; Gennaro, A. L. and Gennaro, A. R. (2000) *Remington: The Science and Practice of Pharmacy*, 20th Ed., Lippincott Williams & Wilkins, Philadelphia, Pa.; Niazi, S. K. (2004) *Handbook of Pharmaceutical Manufacturing Formulations*, CRC Press, Boca Raton, Fla.).

In a second aspect, the present invention relates to a method for preparing a pharmaceutical dosage form as defined herein, the method comprising:

(a) dissolving the tri-substituted glycerol compound in an aqueous excipient; and (b) mixing the dissolved tri-substituted glycerol compound with the aqueous phase of the pharmaceutical dosage form.

The term "aqueous excipient", as used herein, refers to any water-based carrier, diluent or solvent such as water, aqueous buffer solutions and the like. A particularly preferred diluent is water.

The term "aqueous phase", as used herein, denotes the entirety of the water-soluble (i.e. hydrophilic) components of the pharmaceutical dosage form of the invention, that is any active ingredients, excipients, and other adjuvants that are dissolvable in water. If the pharmaceutical dosage form is a gel, particularly a hydrogel, the aqueous phase also comprises one or more gel-forming polymers. In this case, dissolving of the gel-forming polymers may comprise an incubation period upon mixing said polymers with the aqueous excipient in order to allow swelling of the polymers, i.e. the absorption of water. In case the pharmaceutical dosage form is an oil-in-water emulsion, the one or more emulsifiers are preferably added to the aqueous phase.

The dissolving of the tri-substituted glycerol compound and the mixing with the aqueous phase of the pharmaceutical dosage form typically occurs at a temperature between 15° C. and 26° C., preferably between 18° C. and 22° C.

In some embodiments, the inventive method further comprises:

(c) melting the fatty phase of the pharmaceutical dosage form; and (d) adding the aqueous phase of the pharmaceutical dosage form to the fatty phase.

The term "fatty phase" denotes the entirety of the lipid (i.e. hydrophobic or fatty) components of the pharmaceutical dosage form of the invention. The term "melting", as used herein refers to the process of combining any lipid components of the pharmaceutical dosage form and heating the mixture until an homogenous distribution of the different components is achieved. Typically, the melting is performed in a water bath under stirring at a temperature between 30° C. and 85° C., preferably at a temperature between 45° C. and 70° C., and most preferably at a temperature between 55° C. and 65° C.

Subsequently, the aqueous phase and the fatty phase of the pharmaceutical dosage form, respectively, are mixed (typically under continuous stirring) in such a way that the aqueous phase is added to the fatty phase. The aqueous phase may be added at once or successively in two or more parts. Optionally, the aqueous phase is heated to substantially the same temperature as the melted fatty phase prior to adding the aqueous phases to the fatty phase. Typically, the aqueous phase should not be heated to a temperature exceeding 80° C. to avoid evaporation. Stirring of the mixed phases may be continued until the formulation is cooled down to room temperature.

In a third aspect, the invention relates to a tri-substituted glycerol compound, as defined herein, for use as a pharmaceutical dosage form for topical administration.

In preferred embodiments, the tri-substituted glycerol compound, as defined herein, is for the treatment of cancer, wherein the cancer is particularly preferably selected from the group consisting of skin cancer and breast cancer. In specific embodiments, the skin cancer is selected from the group consisting of basal cell carcinoma, squamous cell carcinoma, and malignant melanoma.

In other preferred embodiments, the tri-substituted glycerol compound, as defined herein, is for the treatment of immune diseases, preferably for the treatment of autoimmune diseases.

In a fourth aspect, the invention relates to the use of the pharmaceutical dosage forms, as defined herein, as a medicament for the treatment of cancer or for the treatment of immune diseases.

In a preferred embodiment, the medicament is for the treatment of skin cancer. The term "skin cancer", as used herein, refers to any form of malignant growth of skin cells both of cutaneous (also referred to as dermal) and of subcutaneous (i.e. subdermal) cells. Such malignant cell growth may be manifested by various symptoms including inter alia any skin lesions (wounds, sores, abrasions, and the like) or other changes of the skin that do not heal, ulcers in the skin, discoloring in parts of the skin, and changes in existing moles (i.e. melanocytic nevi).

Preferably, the skin cancer is selected from the group consisting of basal cell carcinoma, squamous cell carcinoma, and malignant melanoma, with the latter one being particularly preferred. These types of skin cancer are reviewed, e.g., in Crowson, A. N. (2006) *Mod. Pathol.* 19 (suppl. 2), S127-S147; Cassarino, D. S. et al. (2006) *J. Cutan. Pathol.* 33, 261-279; Francis, S. O. et al. (2006) *J. Am. Acad. Dermatol.* 55, 849-861; and Miller, A., and Mihm, M. (2006) *N. Engl. J. Med.* 355, 51-65).

In a preferred embodiment, the medicament is for the treatment of breast cancer, in particular for the treatment of subcutaneous metastases from breast cancer. The term "breast cancer", as used herein, refers to any form of malignant growth of breast tissue including ductal carcinoma, lobular carcinoma, inflammatory breast cancer, medullary carcinoma, colloid carcinoma, papillary carcinome, and metaplstic carcinoma. These types of skin cancer are reviewed, e.g., in Loffeld, A., and Marsden, J. R. (2005) *Br. J. Dermatol.* 152, 1206-1210; Karakuzu, A. et al. (2006) *J. Am. Acad. Dermatol.* 55, 1101-1102; and Seidman, A. D. (2006) *Oncology* 20, 983-990.

The term "immune disease", as used herein, refers to any disorder of the immune system. Examples of such immune diseases include inter alia immunodeficiencies (i.e. congenital or acquired conditions in which the immune system's ability to fight infectious diseases is compromised or entirely absent such as AIDS or SCID), hypersensitivity (such as and forms of allergies or asthma), and autoimmune diseases.

In a further preferred embodiment of the present invention, the medicament is for the treatment of autoimmune diseases. Within the scope of the invention, the term "autoimmune disease" is to be understood to denote any disorder arising from an overactive immune response of the body against endogenic substances and tissues, wherein the body attacks its own cells. Examples of autoimmune diseases include inter alia multiple sclerosis, Crohn's disease, lupus erythematosus, myasthenia gravis, rheumatoid arthritis, and polyarthritis.

The invention is further described by the following examples, which are solely for the purpose of illustrating specific embodiments of the present invention, and are not to be construed as limiting the scope of the invention in any way. Materials used in tests below are either commercially available or easily prepared from commercially available materials by those skilled in the art.

EXAMPLES

The methods for preparing the topical pharmaceutical dosage forms according to the present invention follow establish standard methods well known in the pharmaceutical art (see, for example, Niedner, R., and Ziegenmeyer, J. (1997) *Dermatika. Therapeutischer Einsatz, Pharmakologie and Pharmazie.* Wissenschaftliche Verlagsgesellschaft mbH, Stuttgart, Germany; Gennaro, A. L. and Gennaro, A. R. (2000) *Remington: The Science and Practice of Pharmacy*, 20th Ed., Lippincott Williams & Wilkins, Philadelphia, Pa.; Niazi, S. K. (2004) *Handbook of Pharmaceutical Manufacturing Formulations*, CRC Press, Boca Raton, Fla.).

Example 1

Preparation of an Oil-in-Water-Emulsions (Lotion)

For the preparation of an oil-in-water emulsion in form of a lotion the following ingredients were used:

| | |
|---|---|
| 10.0 parts | 1-O-octadecyl-2-O-methyl-glycero-3-phosphocholine |
| 5.0 parts | Lanette ® N (Omikron GmbH; Neckarwestheim, Germany) |
| 5.0 parts | Cetiol ® (Chemos GmbH, Regenstauf, Germany) |
| 80.0 parts | aqua purif. |

1-O-octadecyl-2-O-methyl-glycero-3-phosphocholine is dissolved in water. The fatty phase is melted in a water-bath at a temperature of 60° C. under stirring, and the aqueous phase, optionally pre-warmed to 60° C., is added under stirring. Stirring of the mixed phases may be continued until the formulation is cooled down to room temperature.

Example 2

Preparation of an Oil-in-Water-Emulsions (Lotion)

For the preparation of an oil-in-water emulsion in form of a lotion the following ingredients were used:

| | |
|---|---|
| 12.0 parts | 1-O-octadecyl-2-O-methyl-glycero-3-phosphocholine |
| 2.5 parts | Lanette ® N (Omikron GmbH; Neckarwestheim, Germany) |
| 2.5 parts | Cetiol ® (Chemos GmbH, Regenstauf, Germany) |
| 5.0 parts | paraffin wax subl. |
| 78.0 parts | aqua purif. |

1-O-octadecyl-2-O-methyl-glycero-3-phosphocholine is dissolved in water. The fatty phase is melted in a water-bath at a temperature of 60° C. under stirring, and the aqueous phase, optionally pre-warmed to 60° C., is added under stirring. Stirring of the mixed phases may be continued until the formulation is cooled down to room temperature.

Example 3

Preparation of an Oil-in-Water-Emulsions (Lotion)

For the preparation of an oil-in-water emulsion in form of a lotion the following ingredients were used:

| | |
|---|---|
| 20.0 parts | 1-O-octadecyl-2-O-methyl-glycero-3-phosphocholine |
| 5.0 parts | PEG sorbitan monooleate |
| 35.0 parts | paraffin wax subl. |
| 10.0 parts | wool wax |
| 30.0 parts | aqua purif. |

1-O-octadecyl-2-O-methyl-glycero-3-phosphocholine is dissolved in water. The fatty phase is melted in a water-bath at a temperature of 60° C. under stirring, and the aqueous phase, optionally pre-warmed to 60° C., is added under stirring. Stirring of the mixed phases may be continued until the formulation is cooled down to room temperature.

Example 4

Preparation of an Oil-in-Water-Emulsions (Lotion)

For the preparation of an oil-in-water emulsion in form of a lotion the following ingredients were used:

| | |
|---|---|
| 8.0 parts | 1-O-octadecyl-2-O-methyl-glycero-3-phosphocholine |
| 2.0 parts | Cremophor ® AP solid (BASF, Ludwigshafen, Germany) |
| 1.0 parts | Cremophor ® EL (BASF, Ludwigshafen, Germany) |
| 47.0 parts | olive oil |
| 42.0 parts | aqua purif. |

1-O-octadecyl-2-O-methyl-glycero-3-phosphocholine is dissolved in water. The fatty phase is melted in a water-bath at a temperature of 60° C. under stirring, and the aqueous phase, optionally pre-warmed to 60° C., is added under stirring. Stirring of the mixed phases may be continued until the formulation is cooled down to room temperature.

Example 5

Preparation of an Oil-in-Water-Emulsions (Lotion)

For the preparation of an oil-in-water emulsion in form of a lotion the following ingredients were used:

| | |
|---|---|
| 10.0 parts | 1-O-octadecyl-2-O-methyl-glycero-3-phosphocholine |
| 5.0 parts | PEG sorbitan monostearate |
| 10.0 parts | cetyl alcohol |
| 30.0 parts | peanut oil |
| 10.0 parts | glycerol |
| 35.0 parts | aqua purif. |

1-O-octadecyl-2-O-methyl-glycero-3-phosphocholine is dissolved in water. The fatty phase is melted in a water-bath at a temperature of 60° C. under stirring, and the aqueous phase, optionally pre-warmed to 60° C., is added under stirring. Stirring of the mixed phases may be continued until the formulation is cooled down to room temperature.

Example 6

Preparation of an Oil-in-Water-Emulsions (Lotion)

For the preparation of an oil-in-water emulsion in form of a lotion the following ingredients were used:

| | |
|---|---|
| 20.0 parts | 1-O-octadecyl-2-O-methyl-glycero-3-phosphocholine |
| 1.5 parts | Cremophor ® A6 (BASF, Ludwigshafen, Germany) |
| 1.5 parts | Cremophor ® A25 (BASF, Ludwigshafen, Germany) |
| 3.0 parts | cetyl alcohol |
| 3.0 parts | glycerol monostearate |
| 2.5 parts | 2-octyldodecanol |
| 2.5 parts | triglycerides (middle chain length) |
| 60.0 parts | aqua purif. |

1-O-octadecyl-2-O-methyl-glycero-3-phosphocholine is dissolved in water. The fatty phase is melted in a water-bath at a temperature of 60° C. under stirring, and the aqueous phase, optionally pre-warmed to 60° C., is added under stirring. Stirring of the mixed phases may be continued until the formulation is cooled down to room temperature.

Example 7

Preparation of an Oil-in-Water-Emulsions (Cream)

For the preparation of an oil-in-water emulsion in form of a cream the following ingredients were used:

5-20% (w/w) 1-O-octadecyl-2-O-methyl-glycero-3-phosphocholine in DAC cream basis (according to the German Pharmaceutical Codex)

DAC Cream Basis:

| | |
|---|---|
| 4.0 g | glycerol monostearate 60 |
| 6.0 g | cetyl alcohol |
| 7.5 g | triglycerides (middle chain length) |
| 25.5 g | white vaseline ® (petrolatum) |
| 7.0 g | Macrogol ®-1000-glycerol monostearate |
| 10.0 g | propylene glycol |
| 40.0 g | aqua purif. |

1-O-octadecyl-2-O-methyl-glycero-3-phosphocholine is dissolved in water. The fatty phase is melted in a water-bath at a temperature of 60° C. under stirring, and the aqueous phase, optionally pre-warmed to 60° C., is added under stirring. Stirring of the mixed phases may be continued until the formulation is cooled down to room temperature.

Example 8

Preparation of an Oil-in-Water-Emulsions (Cream)

For the preparation of an oil-in-water emulsion in form of a cream the following ingredients were used:

| | |
|---|---|
| 15.0 parts | 1-O-octadecyl-2-O-methyl-glycero-3-phosphocholine |
| 5.0 parts | Polysorbat ® 60 (BASF, Ludwigshafen, Germany) |
| 10.0 parts | cetyl stearyl alcohol |
| 10.0 parts | 85% (v/v) glycerol |
| 25.0 parts | white vaseline ® (petrolatum) |
| 35.0 parts | aqua purif. |

1-O-octadecyl-2-O-methyl-glycero-3-phosphocholine is dissolved in water. The fatty phase is melted in a water-bath at a temperature of 60° C. under stirring, and the aqueous phase, optionally pre-warmed to 60° C., is added under stirring. Stirring of the mixed phases may be continued until the formulation is cooled down to room temperature.

Example 9

Preparation of an Oil-in-Water-Emulsions (Cream)

For the preparation of an oil-in-water emulsion in form of a cream the following ingredients were used:
1-20% (w/w) 1-O-octadecyl-2-O-methyl-glycero-3-phos-phocholine in *Unguentum emulsificans aquosum*
*Unquentum emulsificans aquosum*:

| | |
|---|---|
| 30.0 parts | emulsifying cetyl stearyl alcohol |
| 35.0 parts | viscous paraffin |
| 35.0 parts | white vaseline ® (petrolatum) |
| plus | aqua purif. in an amount of 1-70% (w/w) |

1-O-octadecyl-2-O-methyl-glycero-3-phosphocholine is dissolved in water. The fatty phase is melted in a water-bath at a temperature of 60° C. under stirring, and the aqueous phase, optionally pre-warmed to 60° C., is added under stirring. Stirring of the mixed phases may be continued until the formulation is cooled down to room temperature.

Example 10

Preparation of an Oil-in-Water-Emulsions (Cream)

For the preparation of an oil-in-water emulsion in form of a cream the following ingredients were used:
1-20% (w/w) 1-O-octadecyl-2-O-methyl-glycero-3-phos-phocholine in *Unguentum alcoholum lanae aquosum*
*Unguentum alcoholum lanae aquosum*:

| | |
|---|---|
| 0.5 parts | cetyl stearyl alcohol |
| 6.0 parts | wool wax alcohol |
| 93.5 parts | white vaseline ® (petrolatum) |
| plus | aqua purif. in an amount of 1-70% (w/w) |

1-O-octadecyl-2-O-methyl-glycero-3-phosphocholine is dissolved in water. The fatty phase is melted in a water-bath at a temperature of 60° C. under stirring, and the aqueous phase, optionally pre-warmed to 60° C., is added under stirring. Stirring of the mixed phases may be continued until the formulation is cooled down to room temperature.

Example 11

Preparation of a Hydrogel

For the preparation of a hydrogel the following ingredients were used:
1-20% (w/w) 1-O-octadecyl-2-O-methyl-glycero-3-phos-phocholine in:

| | |
|---|---|
| 0.5 parts | polyacrylic acid |
| 3.0 parts | 5% (v/v) sodium hydroxide |
| 96.5 parts | aqua purif. |

1-O-octadecyl-2-O-methyl-glycero-3-phosphocholine is dissolved in water. The polyacrylic acid is also dissolved in water. The active ingredient is mixed with the gel-forming polymer and the mixture is incubated at room temperature in order to allow swelling of the polymer. Finally, a neutral pH is adjusted by adding sodium hydroxide.

Example 12

Preparation of a Hydrogel

For the preparation of a hydrogel the following ingredients were used:
1-20% (w/w) 1-O-octadecyl-2-O-methyl-glycero-3-phos-phocholine in:

| | |
|---|---|
| 0.5 parts | polyacrylic acid |
| 5.0 parts | isopropyl alcohol |
| 20.0 parts | polyethylene glycol |
| 1.2 parts | 5% (v/v) sodium hydroxide |
| 73.3 parts | aqua purif. |

1-O-octadecyl-2-O-methyl-glycero-3-phosphocholine is dissolved in water. The polyacrylic acid is dissolved in a mixture of water and polyethylene glycol. The active ingredient is mixed with the gel-forming polymer and the mixture is incubated at room temperature in order to allow swelling of the polymer. Finally, the isopropyl alcohol is added and a neutral pH is adjusted by adding sodium hydroxide.

Example 13

Preparation of a Hydrogel

For the preparation of a hydrogel the following ingredients were used:
1-20% (w/w) 1-O-octadecyl-2-O-methyl-glycero-3-phosphocholine in:

| | |
|---|---|
| 4.0 parts | sodium alginate |
| 10.0 parts | 98% (v/v) glycerol |
| 86.0 parts | aqua purif. |

1-O-octadecyl-2-O-methyl-glycero-3-phosphocholine is dissolved in water. The sodium alginate is dissolved in a mixture of water and glycerol. The active ingredient is mixed with the gel-forming polymer and the mixture is incubated at room temperature in order to allow swelling of the polymer.

Example 14

Preparation of a Hydrogel

For the preparation of a hydrogel the following ingredients were used:
1-20% (w/w) 1-O-octadecyl-2-O-methyl-glycero-3-phosphocholine in:

| | |
|---|---|
| 5.0 parts | sodium carboxymethyl cellulose |
| 10.0 parts | 98% (v/v) glycerol |
| 85.0 parts | aqua purif. |

1-O-octadecyl-2-O-methyl-glycero-3-phosphocholine is dissolved in water. The sodium carboxymethyl cellulose is dissolved in a mixture of water and glycerol. The active ingredient is mixed with the gel-forming polymer and the mixture is incubated at room temperature in order to allow swelling of the polymer.

EMBODIMENTS

1. Pharmaceutical dosage form for topical administration comprising a tri-substituted glycerol compound according to formula (I)

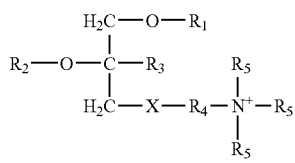

or an enantiomer or diastereomer or a pharmaceutically acceptable salt thereof and at least one pharmaceutically acceptable excipient, wherein
X is selected from the group consisting of phosphate and sulfate;
$R_1$ is selected from the group consisting of $C_{16}$-$C_{20}$ alkyl;
$R_2$ is selected from the group consisting of $C_1$-$C_3$ alkyl and $C_1$-$C_3$ hydroxyalkyl;
$R_3$ is selected from the group consisting of hydrogen and $C_1$-$C_3$ alkyl;
$R_4$ is selected from the group consisting of $C_1$-$C_3$ alkyl and $C_3$-$C_6$ cycloalkyl; and
$R_5$ is selected from the group consisting of hydrogen and methyl.

2. The pharmaceutical dosage form according to embodiment 1, wherein the total amount of lipids in the dosage form is at last 50% (w/w).

3. The pharmaceutical dosage form according to embodiment 2, wherein the total amount of lipids in the dosage form is at last 25% (w/w).

4. The pharmaceutical dosage form according to embodiment 2 or 3, wherein the total amount of lipids in the dosage form is at last 10% (w/w).

5. The pharmaceutical dosage form according to any of embodiments 1 to 4, wherein X is phosphate, $R_1$ is —$(CH_2)_{17}$—$CH_3$, $R_2$ is $CH_3$, $R_3$ is H, $R_4$ is —$(CH_2)_2$—, and $R_5$ is $CH_3$.

6. The pharmaceutical dosage form according to any of embodiments 1 to 5, wherein the total amount of the tri-substituted glycerol compound is at least 5% (w/w).

7. The pharmaceutical dosage form according to embodiment 6, wherein the total amount of the tri-substituted glycerol compound is at least 10% (w/w).

8. The pharmaceutical dosage form according to embodiment 6, wherein the total amount of the tri-substituted glycerol compound is at least 15% (w/w).

9. The pharmaceutical dosage form according to any of embodiments 1 to 8, wherein the dosage form does not comprise liposomes.

10. The pharmaceutical dosage form according to any of embodiments 1 to 9, wherein the dosage form is selected from the group consisting of gels and oil-in-water emulsions.

11. The pharmaceutical dosage form according to embodiment 10, wherein the gel is a hydrogel.

12. The pharmaceutical dosage form according to embodiment 11, wherein the hydrogel comprises one or more gel-forming polymers in a total amount of 0.1% to 15% (w/w).

13. The pharmaceutical dosage form according to embodiment 12, wherein the one or more gel-forming polymers are selected from the group consisting of cellulose derivatives, polyacrylic acid derivatives, tragacanth, and sodium alginate.

14. The pharmaceutical dosage form according to embodiment 10, wherein the oil-in-water-emulsion is selected from the group consisting of creams, lotions, and balms.

15. The pharmaceutical dosage form according to embodiment 14, wherein the oil-in-water emulsion comprises one or more emulsifiers in a total amount of 0.5% to 15% (w/w).

16. The pharmaceutical dosage form according to embodiment 15, wherein the one or more emulsifiers are selected from the group consisting of sorbitan esters, polyoxyethylene sorbitan esters, and glyceryl esters.

17. Tri-substituted glycerol compound as defined in any of embodiments 1 to 16 for use as a pharmaceutical dosage form for topical administration.

18. The tri-substituted glycerol compound according to embodiment 17 for the treatment of cancer.

19. The tri-substituted glycerol compound according to embodiment 18, wherein the cancer is selected from the group consisting of skin cancer and breast cancer.

20. The tri-substituted glycerol compound according to embodiment 17 for the treatment of immune diseases.

21. Method for preparing a pharmaceutical dosage form according to any of embodiments 1 to 16, comprising:
(a) dissolving the tri-substituted glycerol compound in an aqueous excipient; and
(b) mixing the dissolved tri-substituted glycerol compound with the aqueous phase of the pharmaceutical dosage form.

22. The method according to embodiment 21, wherein the aqueous phase of the pharmaceutical dosage form comprises one or more gel-forming polymers.

23. The method according to embodiment 21 or 22, further comprising:
(c) melting the fatty phase of the pharmaceutical dosage form; and
(d) adding the aqueous phase of the pharmaceutical dosage form to the fatty phase.

24. The method according to embodiment 23, wherein the aqueous phase heated to substantially the same temperature as the melted fatty phase prior to mixing said phases.

25. Use of a pharmaceutical dosage form according to any of embodiments 1 to 16 as a medicament for the treatment of cancer.

26. The use according to embodiment 25, wherein the cancer is selected from the group consisting of skin cancer and breast cancer.

27. The use according to embodiment 26, wherein the skin cancer is selected from the group consisting of basal cell carcinoma, squamous cell carcinoma, and malignant melanoma.

28. Use of a pharmaceutical dosage form according to any of embodiments 1 to 16 as a medicament for the treatment of immune diseases.

29. The use according to embodiment 28, wherein the immune diseases are autoimmune diseases.

The present invention illustratively described herein may suitably be practiced in the absence of any element or elements, limitation or limitations, not specifically disclosed herein. Thus, for example, the terms "comprising", "including", "containing", etc. shall be read expansively and without limitation.

Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

All documents cited or referenced herein including any manufacturer's instructions, descriptions, product specifications, and product sheets for any products mentioned herein or in any document referenced herein, are hereby incorporated by reference and may be employed in the practice of the invention. Citation or identification of any document in this application is not an admission that such document is available as prior art to the present invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A method for treating skin cancer or breast cancer, the method comprising administering to a subject in need thereof a topical pharmaceutical dosage form comprising a tri-substituted glycerol compound according to formula (I)

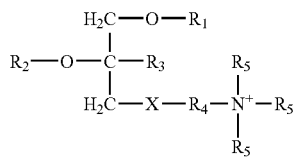

or an enantiomer or diastereomer or a pharmaceutically acceptable salt thereof and at least one pharmaceutically acceptable excipient, wherein X is selected from the group consisting of phosphate and sulfate;

$R_1$ is selected from the group consisting of $C_{16}$-$C_{20}$ alkyl;

$R_2$ is selected from the group consisting of $C_1$-$C_3$ alkyl and $C_1$-$C_3$ hydroxyalkyl;

$R_3$ is selected from the group consisting of hydrogen and $C_1$-$C_3$ alkyl;

$R_4$ is selected from the group consisting of $C_1$-$C_3$ alkyl and $C_3$-$C_6$ cycloalkyl; and $R_5$ is selected from the group consisting of hydrogen and methyl, and wherein the dosage form does not comprise liposomes.

2. The method of treatment according to claim 1, wherein a total amount of lipids in the dosage form is at last 50% (w/w).

3. The method of treatment according to claim 1, wherein X is phosphate, $R_1$ is —$(CH_2)_{17}$—$CH_3$, $R_2$ is $CH_3$, $R_3$ is H, $R_4$ is —$(CH_2)_2$—, and $R_5$ is $CH_3$.

4. The method of treatment according to claim 1, wherein the total amount of the tri-substituted glycerol compound is at least 5% (w/w).

5. The method of treatment according to claim 1, wherein the dosage form is selected from the group consisting of gels and oil-in-water emulsions.

6. The method of treatment according to claim 5, wherein the gel is a hydrogel.

7. The method of treatment according to claim 6, wherein the hydrogel comprises one or more gel-forming polymers in a total amount of 0.1% to 15% (w/w).

8. The method of treatment according to claim 5, wherein the oil-in-water-emulsion is selected from the group consisting of creams, lotions, and balms.

9. The method of treatment according to claim 8, wherein the oil-in-water emulsion comprises one or more emulsifiers in a total amount of 0.5% to 15% (w/w).

10. Method for preparing a topical pharmaceutical dosage form as defined in claim 1, comprising:
(a) dissolving the tri-substituted glycerol compound in an aqueous excipient; and (b) mixing the dissolved tri-substituted glycerol compound with an aqueous phase of the topical pharmaceutical dosage form.

11. The method according to claim 10, wherein the aqueous phase of the topical pharmaceutical dosage form comprises one or more gel-forming polymers.

12. The method according to claim 10, further comprising:
(c) melting a fatty phase of the pharmaceutical dosage form; and
(d) adding the aqueous phase of the topical pharmaceutical dosage form to the fatty phase.

13. The method according to claim 12, wherein the aqueous phase is heated to substantially the same temperature as the melted fatty phase prior to mixing said phases.

14. The method of treatment according to claim 1, wherein a total amount of lipids in the dosage form is at last 25% (w/w).

15. The method of treatment according to claim 1, wherein a total amount of lipids in the dosage form is at last 10% (w/w).

16. The method of treatment according to claim 1, wherein the total amount of the tri-substituted glycerol compound is at least 10% (w/w).

17. The method of treatment according to claim 1, wherein the total amount of the tri-substituted glycerol compound is at least 15% (w/w).

18. The method of treatment according to claim 7, wherein the one or more gel-forming polymers are selected from the group consisting of: cellulose derivatives, polyacrylic acid derivatives, tragacanth, and sodium alginate.

19. The method of treatment according to claim 9, wherein the one or more emulsifiers are selected from the group consisting of: sorbitan esters, polyoxyethylene sorbitan esters, and glyceryl esters.

20. The method according to claim 1, wherein the skin cancer is selected from the group consisting of: basal cell carcinoma, squamous cell carcinoma, and malignant melanoma.

* * * * *